United States Patent [19]

Hayashi et al.

[11] 4,426,718

[45] Jan. 17, 1984

[54] X-RAY DIFFRACTION APPARATUS

[75] Inventors: Makoto Hayashi; Shinji Sakata; Tasuku Shimizu, all of Hitachi, Japan

[73] Assignee: Hitachi, Ltd., Tokyo, Japan

[21] Appl. No.: 296,787

[22] Filed: Aug. 27, 1981

[30] Foreign Application Priority Data

Sep. 1, 1980 [JP] Japan ............................. 55-119774

[51] Int. Cl.³ .......................................... G01N 23/20
[52] U.S. Cl. ..................................... 378/072; 378/86
[58] Field of Search ....................... 378/70, 71, 72, 86

[56] References Cited

U.S. PATENT DOCUMENTS 3,596,092  7/1971  Marjoram ............................. 378/72
3,868,506  2/1975  Ogiso .................................... 378/72

*Primary Examiner*—Paul L. Gensler
*Assistant Examiner*—T. N. Grigsby
*Attorney, Agent, or Firm*—Antonelli, Terry & Wands

[57] ABSTRACT

The X-ray diffraction apparatus of the invention includes means capable of detecting the position and intensity distribution of the diffracted X-ray with respect to a thin bundle X-ray and means for moving the former means to a position at which the former means is capable of detecting the diffracted X-ray, and makes it possible to reliably and easily carry out rough detection of the position of the diffracted X-ray and fine detection of the intensity distribution of the diffracted X-ray without increasing the size of the diffracted X-ray detecting means.

7 Claims, 12 Drawing Figures

X-RAY DIFFRACTION APPARATUS

BACKGROUND OF THE INVENTION

This invention relates to an X-ray diffraction apparatus which radiates a thin bundle of X-rays to a material and detects the diffracted X-rays from the material.

If a thin bundle of X-rays is radiated only to a micros-mall region of a material (such as a spot of about 100 μm, for example), the number of radiated crystal grains and the number of diffracted X-rays from the material can be reduced (to 3 to 5, for example) and hence, the diffracted X-ray for each crystal grain can be detected. The use of such a micro-beam of X-rays leads to the advantage that the crystal structure as well as the degree of strain between the crystal grains can be detected. However, it is difficult to arrange in advance an X-ray detector at a position where it is capable of detecting the diffracted X-rays, because the number of diffracted X-rays is small and their directions are different.

To solve the abovementioned problems, there has conventionally been proposed an apparatus in which a large, semi-circular X-ray detector of the belt-like form is disposed around the radiating position of a small material in such a manner as to cover the anticipated range of angle of the diffracted X-rays (Japanese Patent Laid-Open No. 60843/1980). However, this apparatus is not free from the problem in that the apparatus becomes complicated in construction and large in size and can only be adapted to a small material.

SUMMARY OF THE INVENTION

The present invention is therefore directed to provide an X-ray diffraction apparatus which is compact in construction and is equipped with an X-ray detector capable of easily detecting a thin bundle or micro-beam of X-rays.

It is another object of the present invention to provide an X-ray diffraction apparatus which is equipped with an X-ray detector capable of detecting a wide bundle or conventional beam of X-rays, besides the abovementioned thin bundle of X-rays.

The apparatus in accordance with the present invention includes means capable of detecting the position and intensity distribution of diffracted X-ray and means for moving the former means to a position where the former means is capable of detecting the diffracted X-ray. According to this construction, rough detection of the diffracted X-ray position and fine detection of the intensity distribution of the diffracted X-ray are possible. Hence, the diffracted X-ray detection means can be constructed compactly, and moreover, the diffracted X-ray can be detected accurately and easily.

DESCRIPTION OF THE PREFERRED EMBODIMENTS

Hereinafter, an embodiment of the present invention will be described with reference to the accompanying drawings.

Figure 1:
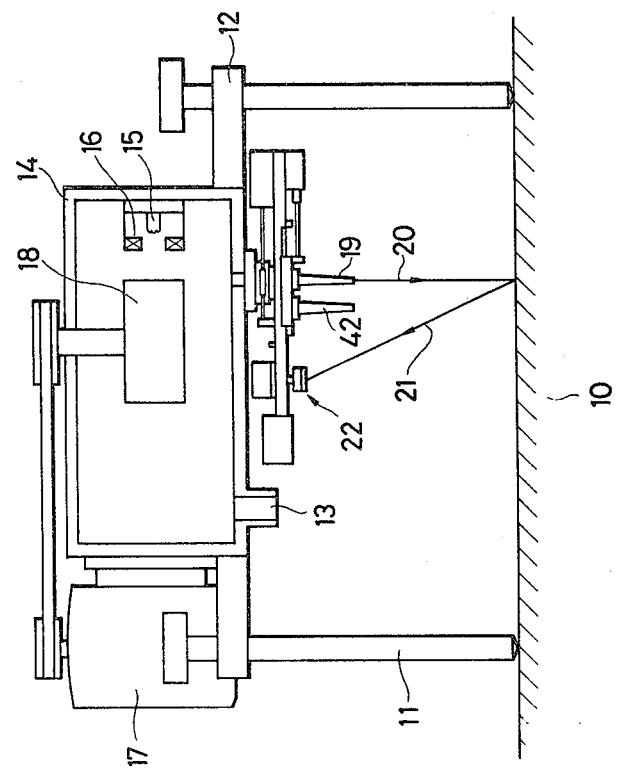
FIG. 1 is a side view of a thin bundle X-ray diffraction apparatus representing an embodiment of the present invention.

FIG. 1 shows the principal portions of an X-ray diffraction apparatus, that is to say, a portion for generating the X-rays and a portion for detecting the diffracted X-rays. These portions are separately constructed from a high voltage power source, a control device and a high vacuum exhaust device, all being not shown in the drawing, so that they can also be adapted to a large-sized structure.

A support 12 is placed on a flat sheet-like material 10 via support legs 11 in such a manner that the vertical position of the support 12 can be adjusted. A vacuum box 14 having a vacuum exhaust port 13 is fitted to this support 12. Inside the vacuum box 14, high speed thermoelectrons generated from a cathode 15 are thinly contracted by an electromagnetic lens 16 disposed around the cathode 15 and impinge against the target of an anode 18 rotated at a high speed by a motor 17, thereby generating the X-rays. The X-rays thus generated pass through a double pin hole 19 for a thin bundle, fitted below the vacuum box 14, are converted into a thin bundle X-ray 20 and are then radiated to the material 10.

Figure 2:
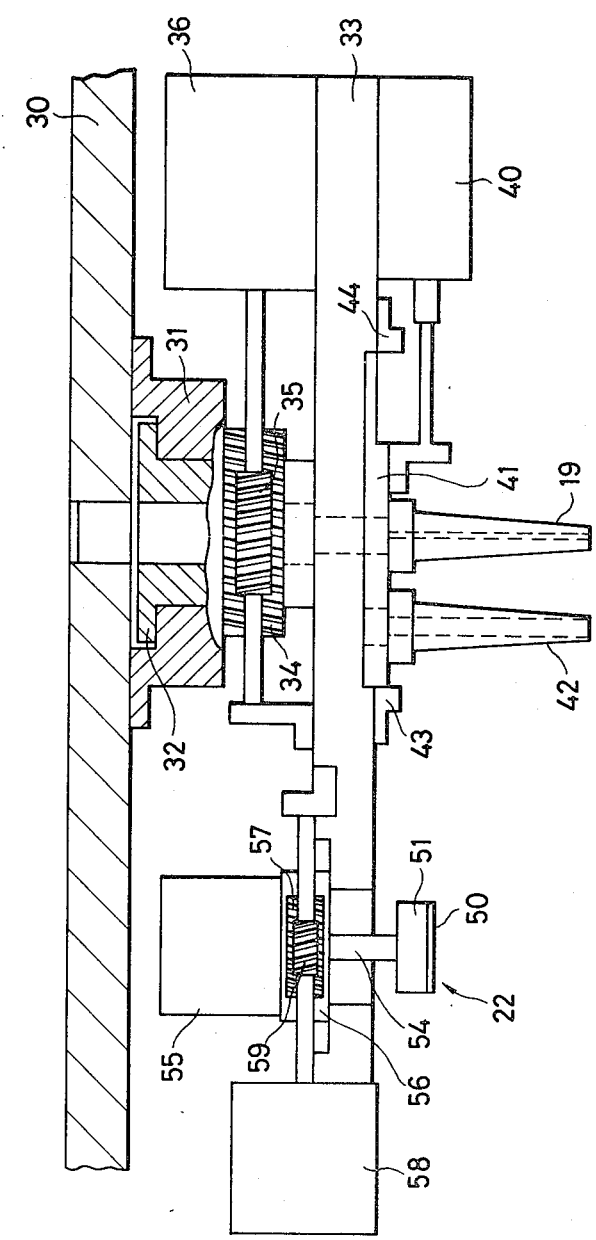
FIG. 2 is a partial sectional view showing the principal portions of FIG. 1.

FIG. 2 is an enlarged view of the principal portions of FIG. 1. A bearing 31 is fixed to a vacuum box base 30, and a cylinder 32 equipped with a revolving plate 33 at its lower portion is suspended from this bearing 31. The revolving plate 33 is allowed to rotate by the combination of a worm gear 34 formed on the surface of the bearing 31 and a worm 35 engaging with this worm gear 34 and rotated by a motor 36 disposed on the revolving plate 33.

Below the revolving plate 33 is disposed a pin hole bed 41 which is allowed by a solenoid 40 to move to the right and left while embracing the revolving plate. Besides the above-mentioned double pin hole 19 for a thin bundle, a double pin hole 42 for a wide bundle is also fixed on this bed 41. Reference numerals 43, 44 represent stoppers that locate the two double pin holes 19, 42 to a rotary shaft of the revolving plate. Namely, it is possible to apply a high voltage to the electromagnetic lens 16 and to generate a high density X-ray by contracting the stream of the thermoelectrons. Furthermore, it is possible to generate a thin bundle or microbeam of X-rays (e.g., 100 to 150 μm) by passing the thermoelectrons through the double pin hole 19 for the thin bundle, or to generate a wide bundle or conventional beam X-ray by applying a low voltage to the electromagnetic lens and passing the thermoelectrons through the double pin hole 42 for the wide bundle (e.g., 500 μm to 1 mm). The application of the wide bundle X-ray will be described elsewhere.

Figure 3:
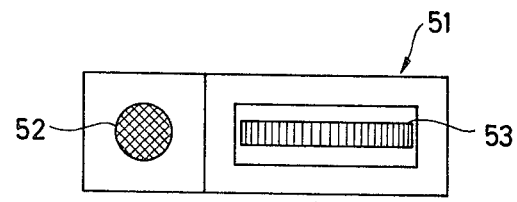
FIG. 3 is a plan view showing the arrangement of a light sensor.

The diffracted X-ray 21 from the material 10 is detected by the X-ray detector 22 consisting of a scintillator 50 for converting the diffracted X-ray into light and a light sensor 51. FIG. 3 is a bottom view in which the light sensor 51 in FIG. 2 is viewed from the bottom to the top. Reference numeral 52 represents a single pin photodiode which is a light sensor having a diameter of a few milimeters and is used to easily detect if the diffracted X-ray exists or not. In other words, this sensor is used for rough detection of the presence of the diffracted X-rays over a large range. Reference numeral 53 represents a silicon photodiode array consisting of some thousands of elements arranged with an about 10 μm pitch in order to increase the position resolution. The array 53 is used for examining the intensity distribution of the diffracted X-ray.

The light sensor 51 is allowed to turn around its own axis by a motor 55 via a shaft 54. Further, the motor 55 is capable of moving towards the double pin holes via a bed 56, that is, in the direction of the turning axis (radial direction) of the revolving plate 33. This movement is effected by the combination of a worm gear 57 disposed on the bed 56 and a worm 59 engaging with the worm gear and rotated by a motor 58.

A method of detecting a diffraction image by use of the X-ray diffraction apparatus having the abovementioned construction will now be described by referring to FIG. 4 which shows a control system. In order to detect a diffraction image of the thin bundle X-ray, the motor 55 is first located so that the longitudinal direction of the photodiode array 53 becomes orthogonal to the radial direction of the revolving plate 33. The single pin photodiode 52 is set by controlling the motor 58 to such a position at which the diffracted X-ray detection is possible. This position is determined by the lattice constants or diffraction plane gap of the material, the wavelength of the X-ray used and the distance between the light sensor and the material. This setting operation may be carried out by applying necessary information from a teletypewriter 60 to a motor control circuit 61 and performing the arithmetic operation by use of a program that is in advance put into this circuit 61.

After the above-mentioned setting is completed, the motor 36 is actuated, thereby causing the single pin photodiode 52 to revolve and scan. If three crystal grains are radiated, for example, the presence of the diffracted X-ray can be detected due to this revolving scanning by a diffraction image position detection circuit 62 at the three positions. Next, the photodiode array 53 is sequentially located at these positions and the diffraction intensity distribution in detail is detected by an intensity distribution circuit 63.

As described above, in accordance with this embodiment, the diffracted X-ray of the thin bundle X-ray can be detected accurately and easily by the compact X-ray detector. As already explained, the wide bundle X-ray can also be radiated to the material in this embodiment. In such a case, if the light sensor 51 is so set by operating the motor 55 that the longitudinal direction of the photodiode array coincides with the radial direction of the revolving plate 33, the half-value width can be measured from the detection information of the photodiode array 53.

Next, a method will be described which method determines the creep life or the life under the action of the creep and fatigue from the diffracted X-ray intensity distribution obtained in the above-mentioned manner.

Figure 5:
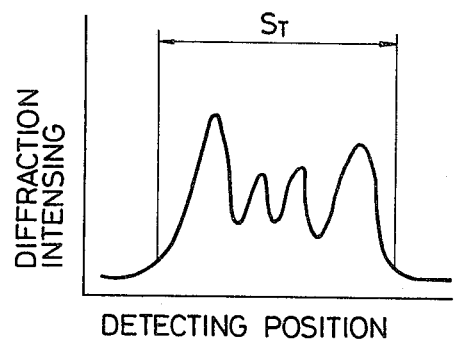
FIG. 5 is a diagram showing the diffraction intensity distribution when a thin bundle X-ray is employed as the incident X-ray.

FIG. 5 shows an example of the diffracted X-ray intensity distribution using the thin bundle X-ray. As can be seen, four peaks occur for one crystal grain. Plural peaks occur for the following reason. Namely, when the material undergoes the tensile strain and the fatigue strain thereby to increase the rearrangement density, the diffraction image expands in the circumferential direction around the axis of the revolving plate (the same as the axis of the pin hole). In this case, since rearrangement gathers and diffuses, crystal subgrains are formed and these subgrains are formed and these subgrains cause the peaks. From the width $S_T$ of the diffraction intensity distribution and the number of peaks m in FIG. 5, the total mis-orientation $\beta$ (the maximum value among the direction of the crystal subgrains) and the diameter t of the subgrains can be determined in the following manner:

$$\beta = 8/\pi \text{ arc sin } (|\tan \theta|/\sin \theta \cdot S_T/4R_O) \quad (1)$$

$$t = t_o m^{-\frac{1}{3}} \quad (2)$$

where $\theta$: Bragg's angle,
$R_o$: distance between light sensor and material,
$t_o$: crystal grain diameter.

Figure 6:
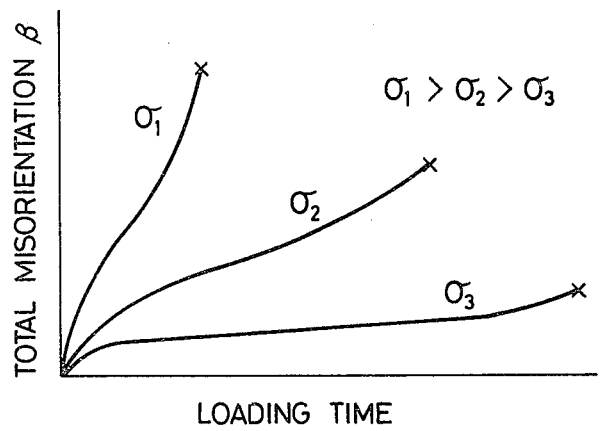
FIG. 6 is a diagram showing the relationship between the total mis-orientation and the loading time.
Figure 7:
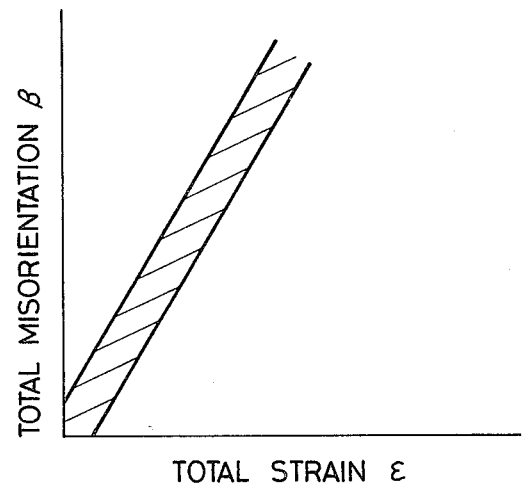
FIG. 7 is a diagram showing the relationship between the total mis-orientation and the total strain.
Figure 8:
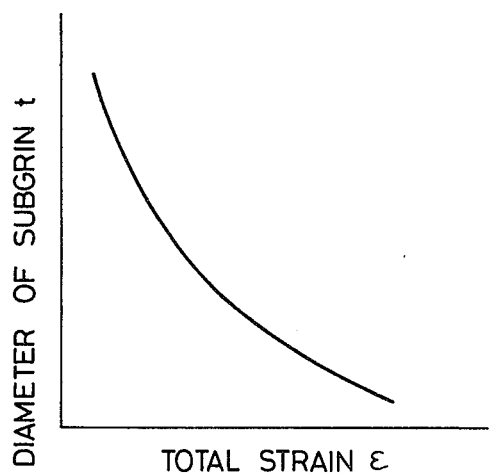
FIG. 8 is a diagram showing the relationship between the diameter of a subgrain and the total strain.
Figure 9:
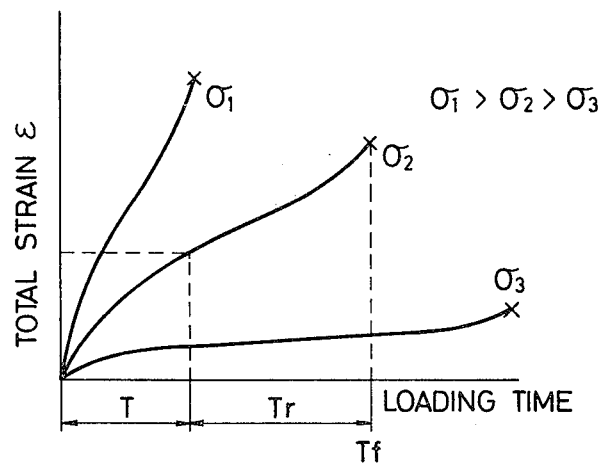
FIG. 9 is a diagram showing the relationship between the total strain and the fatigue life consumption factor.

Since $\beta$ and t correspond to the plastic strain behaviour of a metal, the total strain and the stress amplitude can be estimated by measuring $\beta$ or t. FIG. 6 shows the relationship between the total misorientation $\beta$ and the loading time, and the same relationship is established between the creep strain and the loading time. Accordingly, there is a linear relationship between the total strain $\epsilon$ and the total misorientation $\beta$ such as shown in FIG. 7, the relationship being determined by the material. On the other hand, there is a hyperbolic relationship between the subgrain diameter t and the total strain $\epsilon$ such as shown in FIG. 8. Accordingly, if a master curve of the creep curve at an optional temperature is prepared in advance, the acting stress can be estimated from the total strain $\epsilon$ obtained from FIG. 7 or 8 and from the used time measured actually with reference to FIG. 9. Furthermore, the residual life Tr can be determined by estimating the fracture time Tf at that stress.

Figure 10:
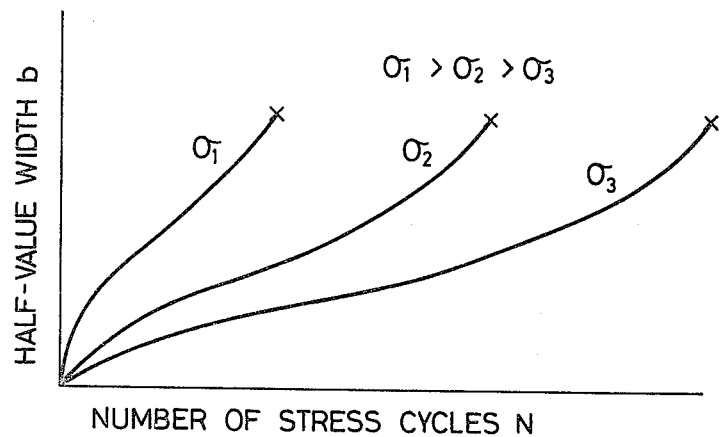
FIG. 10 is a diagram showing the relationship between the half-value width and the number of stress cycles.
Figure 11:
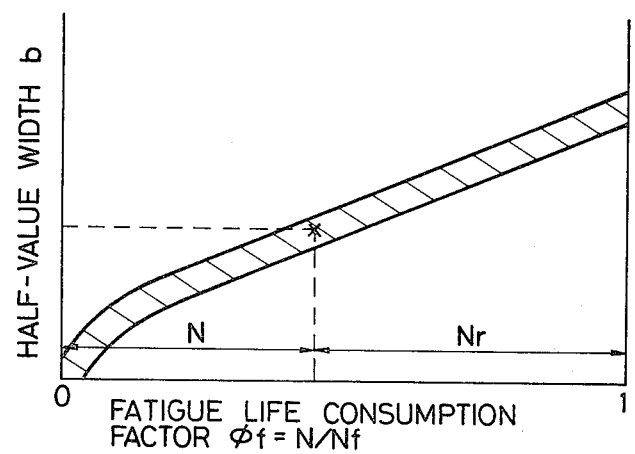
FIG. 11 is a diagram showing the relationship between the half-value width and the fatigue life consumption factor.

Next, a method of obtaining the residual life will be described in such a case where the fatigue and the creep overlap one another. First, the half-value width is measured in accordance with the method that is already described. (Incidentally, the wide bundle X-ray is employed because if the thin bundle X-ray is used, plural peaks occur as shown in FIG. 5 whereby measurement of the half-value width with a high level accuracy is not possible.) There is a relationship between the half-value width b and the number of stress cycles N such as shown in FIG. 10. If this relationship is re-written by plotting the ratio N/Nf between the number of stress cycles N and the number of fracture cycles Nf, a substantially constant relationship can be established such as shown in FIG. 11. Hence, the residual life Nr can be determined by determining the half-value width.

Figure 12:
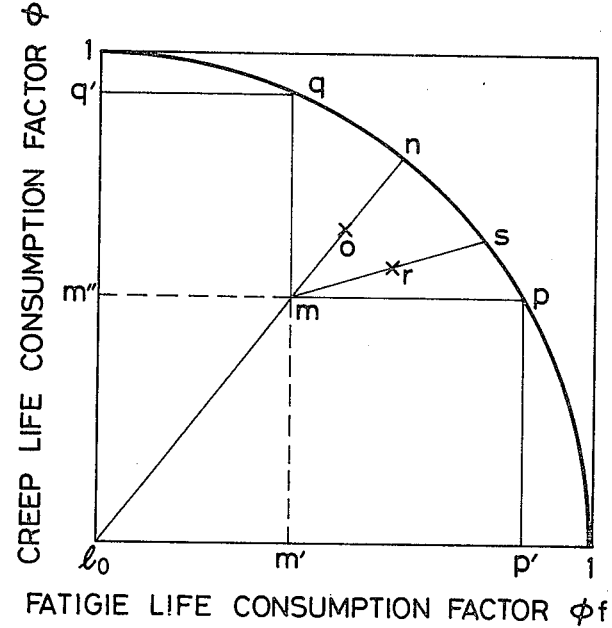
FIG. 12 is a diagram showing the relationship between the creep life consumption factor and the fatigue life consumption factor.

When the fatigue and the creep overlap one another, the creep life consumption factor $\phi_c = T/T_f$ is determined from $\beta$ or t obtained by the thin bundle X-ray method while the fatigue life consumption factor $\phi_f = N/N_f$ is determined from the half-value width b obtained by the wide bundle X-ray method, and $\phi_c$ and $\phi_f$ are then applied to the master curve of the damage curve under overlap of the fatigue and the creep, which curve is obtained in advance in an a laboratory, in order to detect the total damage and to estimate the residual life. In other words, a method of estimating the life using the master curve of the damage curve such as shown in FIG. 12 will be described. First, the operating time T after start of operation and the number of stress cycles N are recorded. Next, the half-value width b, $\beta$ and t are measured at a predetermined inspection time and the life consumption factors $\phi_c$ and $\phi_f$ are obtained from them. $\phi_c$ and $\phi_f$ are plotted on the damage diagram. The origin 1 and the point of damage m are connected by a line, which is further extended to obtain a point of intersection n with the damage curve. Since the time required to reach the damage point m from the origin 1 is T and the number of stress cycles is N, the residual life is given as follows:

$T_r = T \cdot mn/lm$ or $N_r = N \cdot mn/lm$

If T or N is not known, the operation is further continued so as to measure the half-value width b, $\beta$ and t at the time of next predetermined inspection, and the use time T and the number of stress cycles N between these inspections are recorded, thereby obtaining the residual life expressed by the following equation:

$T_r = T \cdot on/mo$ or $N_r = N \cdot on/mo$

When the operating condition changes from the damage point m and only the fatigue is applied, the residual life Nr can be obtained from the following equation by drawing a line from the point m in parallel to the $\phi_f$ axis to plot the point of intersection p with the damage curve, and drawing perpendicularly lines from the points m and p to the $\phi_f$ axis to obtain the points of intersection m' and p', respectively:

$Nr = N \, m'p'/lm'$

Similarly, $Tr = m''q'/lm''$ represents the residual life when only the creep is applied from the damage point m.

If the fatigue and the creep are applied in the overlap state from the damage point m, the used time T and the number of stress cycles N are recorded to measure the half-value width b, $\beta$ and t, and when the degree of damage reaches the point r, the residual life can be obtained from $Nr = N \, rs/mr$ or $Tr = T \, rs/mr$ with s representing the point of intersection between an extension of mr and the damage curve.

In this manner, the creep life, the fatigue life and the residual life when the creep and the fatigue overlap one another can be estimated.

Figure 4:
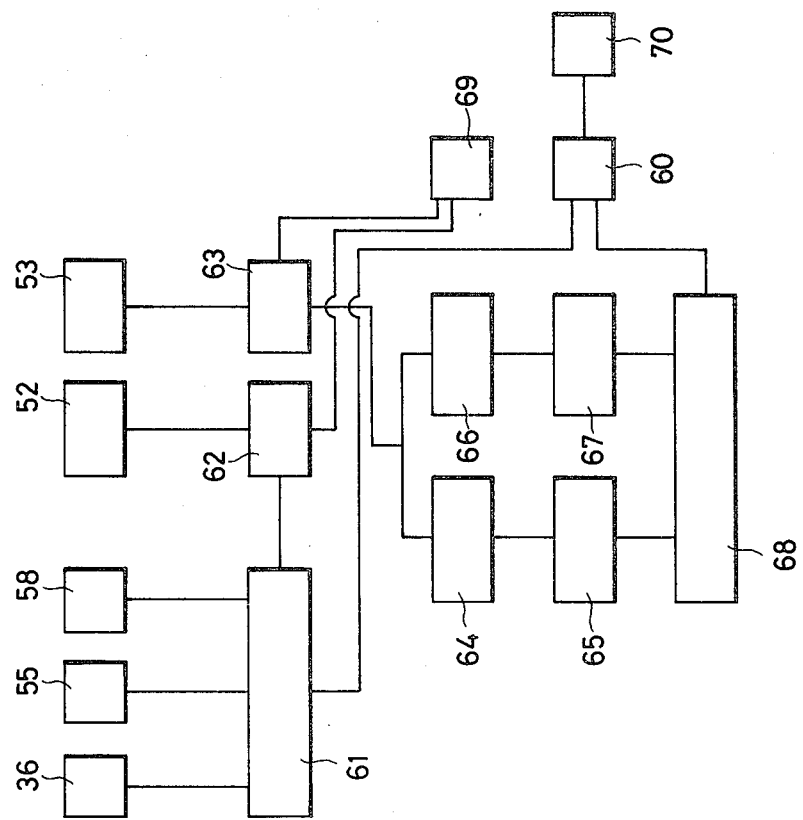
FIG. 4 is a block diagram showing a control system of the X-ray diffraction apparatus.

The estimation method of the residual life described above can be accomplished by the control system shown in FIG. 4.

The total misorientation $\beta$ and the subgrain diameter t obtained by a measuring circuit 66 for the misorientation and subgrain diameter are applied to a creep damage measuring circuit 67. This circuit 67 memorizes creep curves at each temperature that are obtained in advance by experiments, and compares the total strain obtained from $\beta$ or t with the temperature and time T used that are applied from the tele-typewriter 60, thereby obtaining the stress and calculating the creep life consumption factor $\phi_c = T/T_f$ as well as the residual life Tr.

The half-value width b obtained by a half-value width measuring circuit 64 is applied to a fatigue damage judging circuit 65. This circuit 65 memorizes in advance the master curves of the half-value width change at each temperature and compares the master curve with b, thereby calculating the fatigue life consumption factor $\phi_f = N/N_f$ and the residual life Nf using the number N of stress cycles applied thereto from the tele-typewriter 60.

When the creep and the fatigue overlap one another, the creep life consumption factor $\phi_c$ and the fatigue life consumption factor $\phi_f$ are applied to the life judging circuit 68 and are compared with the damage curves that are stored in a memory of this circuit 68, thereby calculating the residual life Tr and Nr in the above-mentioned manner. The results of calculation are applied to the tele-typewriter 60. The various information thus obtained may be displayed on a display 69 or a plotter 70.

What is claimed is:

1. An X-ray diffraction apparatus comprising: means for radiating a micro-beam of X-rays to a material; means capable of detecting the position and intensity distribution of diffracted X-ray from said material; means for obtaining the total misorientation or the diameter of a crystal subgrain on the basis of a signal of said diffracted X-ray detecting means; and means for obtaining the creep life consumption factor of said material from the relationship between the total strain and the loading time under the creep state that is in advance obtained for the same material.

2. The X-ray diffraction apparatus as defined in claim 1 wherein said diffracted X-ray detecting means comprises a first sensor for detecting the position of the diffracted X-ray and a second sensor for detecting the intensity distribution of the diffracted X-ray and is equipped with means for rotating said diffracted X-ray detecting means on its own axis and around an axis parallel to the radiating direction of the X-ray; said rotating means comprising means for rotating said diffracted X-ray detecting means around said micro-beam of X-rays and means for changing the gap between the axis of rotation of said rotating means and said diffracted X-ray detecting means; said first sensor comprising a single photodiode and said second sensor comprising an elongate array of photodiodes which are juxtaposed next to each other; and said means for rotating said diffracted X-ray detecting means on its own axis is so controlled, when said second sensor detects the intensity distribution of the diffracted X-ray, that the longitudinal direction of said photodiode array is orthogonal to the radial direction of said rotating means for rotating said diffracted X-ray detecting means around said micro-beam of X-rays.

3. The X-ray diffraction apparatus as defined in claim 2 wherein said means for radiating said micro-beam of X-rays comprises a cathode for generating thermoelectrons, an electromagnetic lens capable of adjustably contracting the stream of thermoelectrons impinging against an anode and a micro-beam double pin hole for allowing the passage of the X-ray generated from said anode therethrough and is equipped with a conventional beam double pin hole for obtaining a conventional beam of X-rays and with means for moving said double pin holes so that the holes of both of said double pin holes coincide with the axis of rotation of said rotating means; said second sensor detects the intensity distribution of the diffracted X-ray with respect to said conventional beam X-ray under the state in which the longitudinal direction of said photodiode array coincides with the radial direction of said rotating means; and said X-ray diffraction apparatus further includes means for obtaining a half-value width on the basis of the detection signal of said second sensor, means for obtaining the fatigue life consumption factor with respect to the fatigue damage from the relationship between the ratio of the half-value width obtained in advance for the same material, the number of stress cycles and the number of fracture cycles on the basis of the signal of said half-value width operating means; and means for obtaining the residual life under the action of the fatigue and the creep from said fatigue life consumption factor and said creep life consumption factor.

4. An X-ray diffraction apparatus for irradiating a material with X-rays and detecting the X-rays diffracted therefrom, comprising means for radiating a bundle of X-rays to said material, said means for radiating including changing means for selectively providing said bundle in the form of either a micro-beam or a conventional beam of X-rays, means for detecting diffracted X-rays, said detecting means comprising a first sensor for detecting the position of the diffracted X-rays and a second sensor for detecting the intensity distribution of diffracted X-rays, means for rotating said detecting means about the axis of the X-ray beam applied to said material, means for moving said detecting means in a radial direction with respect to the axis of said X-ray beam, and means for rotating said detectng means about its own axis.

5. The X-ray diffraction apparatus as defined in claim 4, wherein said first sensor is a single photodiode and said second sensor is an elongate array of photodiodes which are juxtaposed next to each other.

6. The X-ray diffraction apparatus as defined in claim 5, wherein said means for rotating said diffracted X-ray detecting means on its own axis is so constructed that at least the longitudinal direction of the photodiode array of said second sensor can be arranged in a tangential or a radial direction with respect to a circular path along which said detecting means is moved when rotating about the axis of the X-ray beam applied to said material.

7. The X-ray diffraction apparatus as defined in claim 5, wherein said means for radiating a bundle of X-rays to said material comprises a cathode for generating thermoelectrons, and electromagnetic lens capable of adjustably contracting the stream of thermoelectrons impinging against an anode and a double pin hole for allowing the passage of a bundle of X-rays generated from said anode therethrough, said double pin hole being one of a micro-beam double pin hole and a conventional beam double pin hole, and wherein said changing means for selectively providing said bundle of X-rays in the form of either a micro-beam or a conventional beam of X-rays comprises means for moving said double pin holes so that the holes of a selected one of said double pin holes coincide with the axis of rotation of said rotating means.

* * * * *